United States Patent
Fujisato et al.

(10) Patent No.: US 8,415,125 B2
(45) Date of Patent: Apr. 9, 2013

(54) METHOD FOR PREPARING BIOLOGICAL SCAFFOLD MATERIAL

(75) Inventors: Toshiya Fujisato, Suita (JP); Dohiko Terada, Suita (JP); Kazuya Sawada, Suita (JP); Takeshi Nakatani, Suita (JP)

(73) Assignee: Japan Health Sciences Foundation, Chuo-ku, Tokyo (JP)

( * ) Notice: Subject to any disclaimer, the term of this patent is extended or adjusted under 35 U.S.C. 154(b) by 0 days.

(21) Appl. No.: 12/090,197

(22) PCT Filed: Oct. 10, 2006

(86) PCT No.: PCT/JP2006/320181
§ 371 (c)(1),
(2), (4) Date: Oct. 6, 2009

(87) PCT Pub. No.: WO2007/043513
PCT Pub. Date: Apr. 19, 2007

(65) Prior Publication Data
US 2010/0021961 A1    Jan. 28, 2010

(30) Foreign Application Priority Data
Oct. 14, 2005 (JP) ................................ 2005-299590

(51) Int. Cl.
*C12N 9/00* (2006.01)
*A61K 38/17* (2006.01)

(52) U.S. Cl.
USPC .......................................... 435/183; 530/353

(58) Field of Classification Search ........................ None
See application file for complete search history.

(56) References Cited

U.S. PATENT DOCUMENTS 4,378,224 A * 3/1983 Nimni et al. ................... 8/94.11
4,399,123 A * 8/1983 Oliver et al. .................. 424/570

FOREIGN PATENT DOCUMENTS

JP    2000-516489 A    12/2000

OTHER PUBLICATIONS

Muto et al., "Modified Vein Allograft for Small Arterial Reconstruction in Dogs", Jpn. J. Surg., 1986, 16(3):225-230.*
Balo et al., "The Elastolytic Activity of Pancreatic Extracts", Biochem. J., 1959, 46:384-387.*
Lu et al., "Novel porous aortic elastin and collagen scaffolds for tissue engineering", Biomaterials 25 (2004) 5227-5237.*
Muto, Y. et al., "Modified vein allograft for small arterial reconstruction in dogs," Japan J. Surg., 1986, vol. 16 No. 3, pp. 225-230.
Vyavahre, N. et al., "Elastin calcification and its prevention with aluminum chloride pretreatment," Am. J. Pathol., 1999, vol. 155 No. 3, pp. 973-982.
Bailey, M.T. et al., "Role of elastin in pathologic calcification of xenograft heart valves," J. Biomed. Mater Res. A., 2003, vol. 66 No. 1, pp. 93-102.
International Search Report dated Dec. 15, 2006 of International Application No. PCT/JP2006/320181 filed Oct. 10, 2006.

* cited by examiner

*Primary Examiner* — Suzanne M Noakes
(74) *Attorney, Agent, or Firm* — Millen, White, Zelano, Branigan, P.C.

(57) ABSTRACT

Disclosed is a method for production of a bio-derived scaffold for use in regenerative medicine, which has a bio-compatibility and biodegradability and can self-organize and grow without causing calcification. The method comprises the steps of partially fixing a biological soft tissue with glutaraldehyde by cross-linking and incubating the partially fixed tissue together with an elastase.

6 Claims, 3 Drawing Sheets

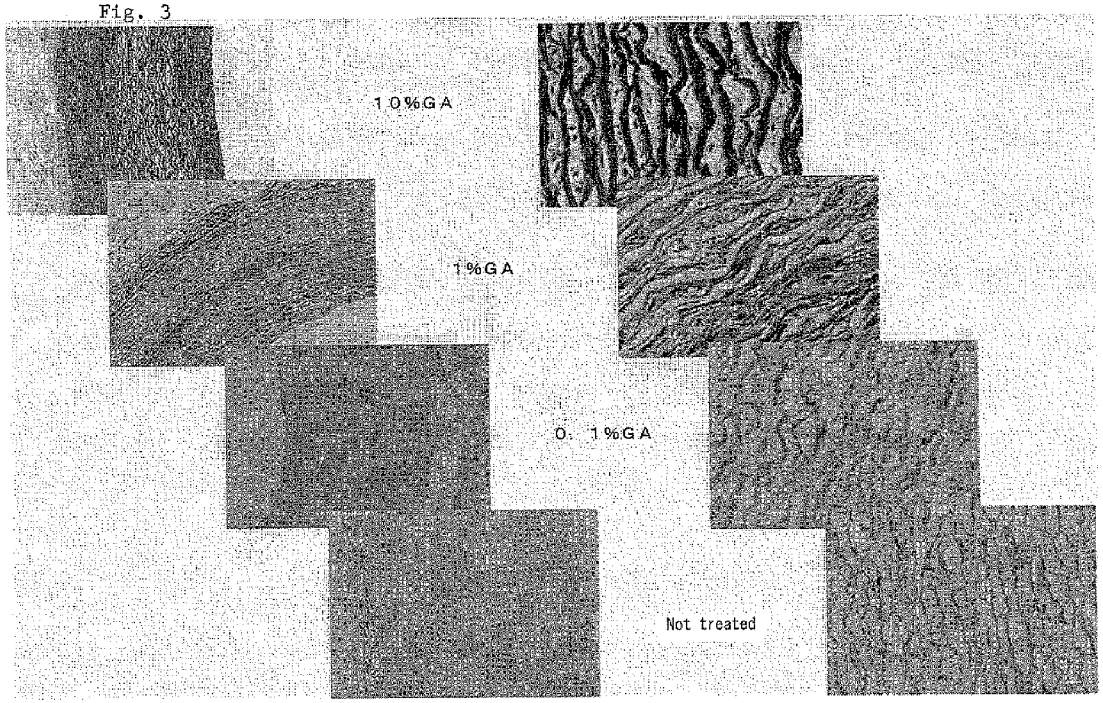

METHOD FOR PREPARING BIOLOGICAL SCAFFOLD MATERIAL

FIELD OF THE INVENTION

The present invention relates to regenerative medical technology. Particularly, it relates to a method for preparing biological scaffold materials made of soft tissues of mammalian origine.

BACKGROUND ART

Prosthetic surgery is aimed to repair impaired organs by replacing with artificial devices or by grafting artificial or native scaffolds for developing into autogenic tissues. Currently more than 10,000 patients undergo heart valve replacement surgery in Japan. Mechanical valves are used in about 7% of the patients and xenogenic valves made from glutaraldehyde-fixed porcine or bovine tissues are used in the balance of patients. In case of mechanical valves, continuous administration of an antithrombotic agent is essential after replacement while affecting patient's quality of life. The xenogenic valves are durable in vivo only for about 15 years due to calcification and requires repeated replacement surgery for young generation.

In case of glutaraldehyde-fixed xenogenic vascular grafts, there exists, in addition to the limited durability due to calcification, another disadvantage. Namely inherent mechanical properties such as tensile strength and elasticity possessed by the native tissue have been lost. Artificial vascular grafts made of biodegradable polymers such as polylactic acid have been clinically used in the venous system of children. However, restenosis and other adverse effects have been reported. In addition, the biodegradable vascular grafts cannot be used in the arterial system because of possible puncture due to the hydrolysis of the polymer.

It is known to prepare scaffold materials for grafting by decellularizing native tissues with enzymes or detergents to obtain extracellular matrix components. However, the decellularized tissues as such do not have a strength sufficient to withstand relatively high pressures required as, for example, the aortic valve. Thus some strengthening treatment such as cross-linking with glutaraldehyde is indispensable. The fixation with glutaraldehyde, however, necessarily diminishes the biodegradability of matrix collagen and the treated tissue thus remains unchanged in the living body such that ingrowth of autogenic cells, which is essential for the regeneration of autogenic tissues, hardly takes place.

JP 5404388B corresponding to U.S. Pat. No. 4,098,571 discloses a process for preparing a xenograft blood vessel substitute comprising enzymatically digesting a porcine blood vessel with chymotrypsin and then fixing the resulting digested blood vessel with a fixing agent such as glutaraldehyde. This blood vessel substitute is intended to use as an artery-vein shunt for accessing to the vascular system of those patients who undergo long term hemodialysis. In this case, ingrowth of patient's own cells into the grafted blood vessel is not essential.

Accordingly, a need remains to exist for a biological scaffold material which is biocompatible in terms of immunogenicity and thrombogenicity, which may be eventually decomposed in the living body but persistent until it is incorporated into the recipient's own tissue, and which allows ingrowth of autogenic cells without calcification.

DISCLOSURE OF THE INVENTION

According to the present invention, the above need may be met by providing a method for preparing an implantable scaffold material comprising the steps of:

(a) partially cross-linking and fixing a native soft tissue with glutaraldehyde, and (b) incubating the resulting tissue with elastase to selectively remove elastin therefrom.

BRIEF DESCRIPTION IS DRAWINGS

FIG. 3 shows histographic pictures of porcine aorta segments stained by the Elastica von Gieson method before and after treating with varying concentrations of glutaraldehyde followed by incubation with elastase.

DETAILED DISCUSSION

Figure 1:
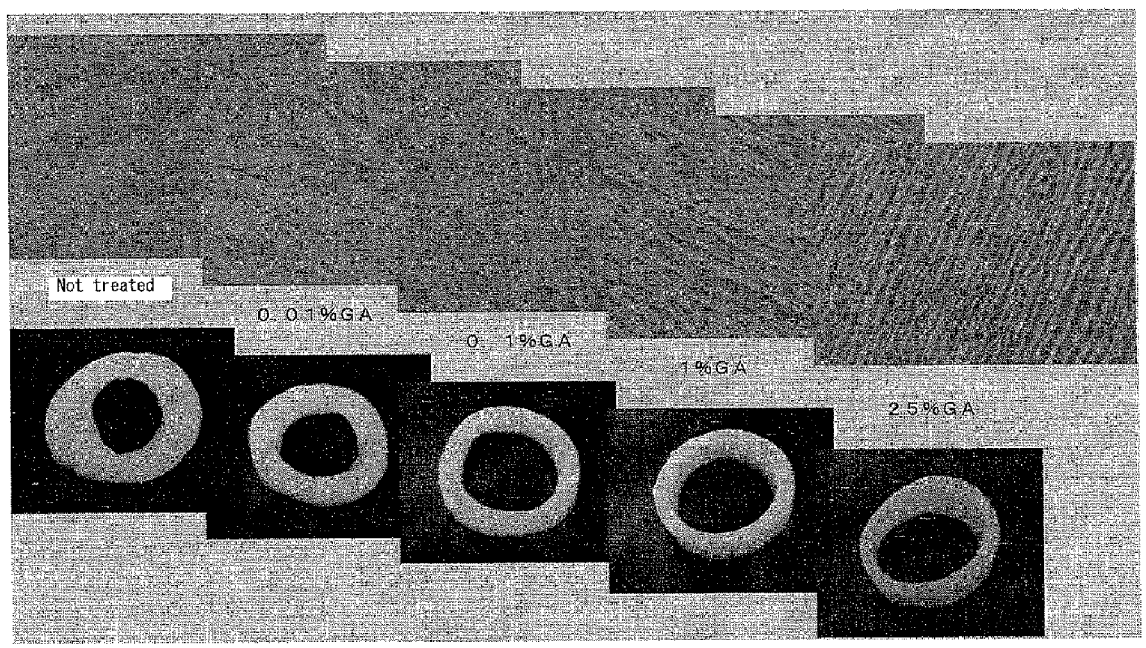
FIG. 1 shows photographs of appearance and histographic pictures of porcine aorta segments before and after treating with varying concentrations of glutaraldehyde followed by incubation with elastase.

The present invention has its basis on the fact that elastin is involved in the calcification of scaffold materials derived from native tissues. However, removal of elastin alone is not sufficient to produce a scaffold material having other requisite properties such as satisfactory mechanical strength and thus requires conjunctive use of partial fixing with glutaraldehyde.

Generally fixation of a native tissue with glutaraldehyde is performed by immersing the tissue in an aqueous solution of glutaraldehyde for a sufficient period of time at which no longer the reaction takes place. The tissue thus treated is neither susceptible to degradation in vivo nor available to digestion by proteolytic enzymes because structural proteins therein have been completely denatured to an insoluble state. However, it is possible to retain the susceptibility to enzymatic degradation of the tissue by controlling the extent of fixation with glutaraldehyde.

Elastin is a hard protein forming connecting tissues, outer wall of aorta and other hard tissues of higher animals. Elastin is consisted mainly of electrically neutral non-aromatic amino acid residues. Glutaraldehyde reacts mainly with lysine residues to cross-link proteins inter- and intramolecularly. Glutaraldehyde is thus hardly capable of cross-linking elastin which is essentially free from lysine residues. Accordingly, elastin may be selectively removed from partially cross-linked tissues with glutaraldehyde utilizing the substrate-specificity.

The extent of cross-linking of the tissue with glutaraldehyde is a function of its concentration when the reaction temperature is constant. U.S. Pat. No. 4,378,224 discloses a method for preparing a scaffold from mammalian tissues. The method comprises treating the tissue with glutaraldehyde solution at a concentration between about 0.05 wt. % and about 0.4 wt. %, preferably about 0.15 wt. %, for between about 12 and about 64 hours, preferably following by cross-linking the tissue with an aliphatic diamine using a carbodiimide. According to our studies, the partial cross-linking with glutaraldehyde may be optimized by immersing the tissue in a glutaraldehyde solution at a concentration of 0.1 wt. % for about one hour at room temperature. However, a comparable level of partial cross-linking may be achieved by immersing the tissue in a glutaraldehyde solution at a concentration higher than 0.1 wt. % for less than 1 hour or in a glutaraldehyde solution at a concentration lower than 0.1 wt. % for more than 1 hour since the level of partial cross-linking is, as stated above, a function of the concentration of glutaraldehyde and the length of reaction time.

The selective removal of elastin from the partially cross-linked tissue may be carried out in a buffer solution at an optimum pH of the enzyme. We have obtained a satisfactory result by incubating in a Tris buffer at pH 8.0 at 37° C. It is, of course, within the scope of the present invention to carry out the incubation step in other buffer solutions at a pH recommended by the supplyer of elastase, for example, between pH 7.5 and pH 8.5. The concentration of the enzyme is generally between 300 and 1,000 U/L, preferably about 600 U/L. The incubation time is from 1 day to 1 week, preferably between 2 and 7 days at 37° C.

After the incubation step, the tissue may be rinsed with water, physiological saline or a buffer and stored in a preserving solution such as PBS until use.

EXAMPLES

In the following examples, native porcine aorta tissues purchased from Japan Farm Co., Ltd. were treated with glutaraldehyde (herein after "GA") under varying conditions and then incubated under a constant condition in 0.01 M Tris buffer, pH 8.0 containing 150 mg/L of elastase (3.95 U/mg, Funakoshi) (577.5 U/L) for 4 days at 37° C.

Example 1

Porcine aorta tissue segments were treated with 0.01% GA, 0.1% GA, 1% GA and 25% GA, respectively, at room temperature for 1 hour, and then subjected to enzymatic degradation of elastin under the above constant condition. As a control, a tissue segment not treated with GA was also subjected to the enzymatic degradiation of elastin under the same conditions. FIG. 1 shows in the photographs in the lower row appearance of annularly cut aorta segments and histographic pictures of the tissue segment stained with hemotoxilin-eosin in the upper row. As shown in FIG. 1, untreated tissue and treated tissue with 0.01% GA were excessively loosened by the enzymatic removal of elastin and did not retain the original shape. In contrast, the tissues treated with 1% GA and 25% GA, respectively, were observed to contain an amount of elastin sufficient to retain the original shape after the treatment with the enzyme due to partial cross-linking with GA. Essentially complete removal of elastin while retaining the original shape was observed with the treatment of 0.1% GA. Denucleation of donor cells was also observed in this case.

Example 2

Figure 2:
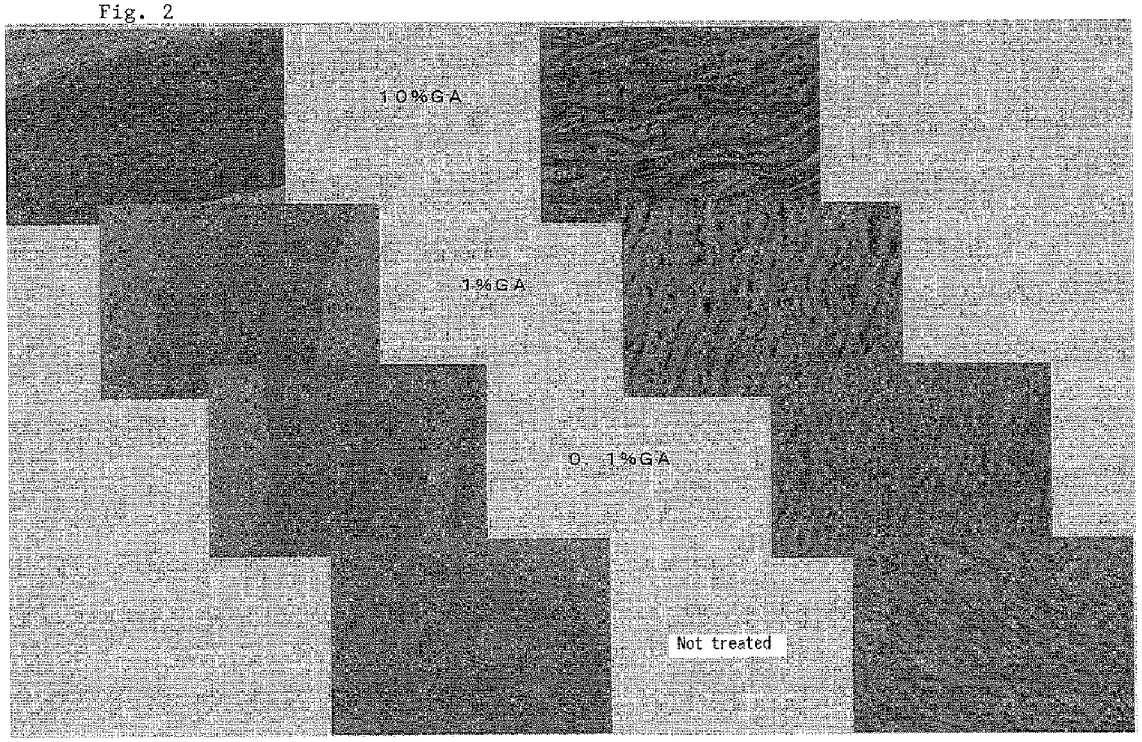
FIG. 2 shows histographic pictures of porcine aorta segments stained with hemotoxylin-eosin before and after treating with varying concentrations of glutaraldehyde followed by incubation with elastase.

As in Example 1, porcine aorta tissue segments were treated with GA at varying concentrations from 0% to 25%, and then subjected to enzymatic degradation of elastin. Cytographic pictures were taken after staining hemotoxylin-eosin at different enlargement scales. As shown in FIG. 2, excessive loosening of the tissue was observed in the tissue not treated with GA. In the tissue treated with 1% GA or 10% GA, many elastin fibers and cell nuclei were observed.

Example 3

Porcine aorta tissue segments were treated with GA and elastase under the same conditions as in Example 2, and the stained by the Elastica von Gieson method, FIG. 3 shows enlarged histographic pictures of tissues thus treated. According to the above staining method, collagen fibers appear significantly darker than elastin fibers in monochromatic photographs. As observed from the pictures, residual elastin fibers increased with increase in GA concentration.

The tissue segment treated with 0.1% GA in Example 2 was digested with collagenase (228 U/mg, Wako Pure Chemical) in tris-buffer and the digested solution was analyzed spectroscopically. An absorption near 280 nm responsible for aromatic amino acids was observed indicating the biodegradability of the scaffold produced by the method according to the present invention.

As a result of the foregoing experiments, the effect of the treatment of a native tissue with glutaraldehyde under appropriate conditions before removing elastin by the enzymatic action has been confirmed. Namely, the above treatment enables to provide a scaffold for regenerative medical procedures which retains the physical shape and flexibility of the starting native tissue and which is porous for allowing ingrowth of cells.

The invention claimed is:

1. A method for preparing an implantable scaffold material comprising the steps of:
    (a) partially cross-linking and fixing a native soft tissue with glutaraldehyde, and
    (b) subsequently incubating the resulting tissue from step (a) with elastase to selectively remove elastin therefrom.

2. The method according to claim 1 wherein said step (a) is carried out by immersing the tissue in an aqueous solution of glutaraldehyde at a concentration of 0.1 wt. % or less for a period of time not more than 5 hours.

3. The method according to claim 2 wherein the tissue is immersed in an aqueous solution of glutaraldehyde at a concentration of 0.1 wt. % for 1 hour at room temperature.

4. The method according to claim 1 wherein said step (b) is carried out in a buffer solution at an optimum pH of elastase.

5. The method according to claim 4 wherein said step (b) is carried out in Tris buffer at a pH between 7.5 and 8.5.

6. The method according to claim 1 further comprising washing the tissue after the step (b).

* * * * *